United States Patent
Lin et al.

(10) Patent No.: US 7,020,536 B2
(45) Date of Patent: Mar. 28, 2006

(54) METHOD OF BUILDING A DEFECT DATABASE

(75) Inventors: Long-Hui Lin, Hsin-Chu Hsien (TW); Feng-Ming Kuo, Tao-Yuan Hsien (TW); Su-Fen Cheng, Tainan Hsien (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 0 days.

(21) Appl. No.: 10/708,059

(22) Filed: Feb. 6, 2004

(65) Prior Publication Data

US 2005/0177264 A1   Aug. 11, 2005

(51) Int. Cl.
 *G06F 19/00*   (2006.01)
(52) U.S. Cl. ..................... 700/110; 707/102
(58) Field of Classification Search ............. 700/110; 707/102; 717/106
See application file for complete search history.

(56) References Cited

U.S. PATENT DOCUMENTS

| | | | |
|---|---|---|---|
| 6,512,842 B1* | 1/2003 | Steffan et al. | 382/149 |
| 6,643,006 B1* | 11/2003 | Hsu et al. | 356/237.2 |
| 6,826,298 B1* | 11/2004 | O'Dell et al. | 382/149 |

* cited by examiner

*Primary Examiner*—Leo Picard
*Assistant Examiner*—Sheela S. Rao
(74) *Attorney, Agent, or Firm*—Winston Hsu

(57) ABSTRACT

First, a wafer with a plurality of defects generated in a first semiconductor process is provided. A defect inspection is performed to detect the defects on the wafer. Then, an automatic defect classification is performed according to a predetermined defect database having a defect classification recipe generated from a second semiconductor process. After that, a verifying process is further performed by comparing the result of the automatic defect classification with that of a manual defect classification to verify the accuracy of the automatic defect classification.

8 Claims, 3 Drawing Sheets

METHOD OF BUILDING A DEFECT DATABASE

BACKGROUND OF INVENTION

1. Field of the Invention

The present invention relates to a method of building a defect database, and more particularly, to a method of building a defect database applied to an automatic defect classification system.

2. Description of the Prior Art

In the semiconductor fabricating process, some small particles and defects are unavoidable. As the size of devices shrinks and the integration of circuits increases gradually, those small particles or defects affect the property of the integrated circuits more seriously. For improving the reliability of semiconductor devices, a plurality of defect detections are performed continuously, and the detected defects are further examined for analyzing a root cause of the defects. According to the result of the defect root cause analysis, process parameters are tuned correspondingly to reduce a presence of defects or particles so as to improve the yield and reliability of the semiconductor fabricating process.

Please refer to FIG. 1, which is a schematic diagram of a prior art method of a defect detection and analysis process. As shown in FIG. 1, a sampling 12 is first performed to obtain a test sample for inline product wafers. Then, a defect inspection 14 is performed according to the test sample. In the defect inspection 14, a large scale of scan is typically performed to detect defects roughly. After that, a defect review 18 is performed to examine the detected defects in detail by some proper machines such as an SEM and a defect root cause analysis 22 is performed according to a result of the defect review 18. Since the defect review 18 is a heavy loading and time-consuming work, it is impossible to perform a defect review 18 for all detected defects. Typically, a sampling for selecting some defects is required to perform the defect review 18. Normally, a defect classification 16 is performed after finishing the detect inspection 14, to separate the defects into different defect types. Then, a certain amount of defects of each defect type are picked up for the defect review 18 and the following defect analysis 22, to find the root cause of the defects. Therefore, the defect generation can be reduced by tuning process parameters properly.

In the prior art technology, most of the defect classification 16 is manual work. Thus, much effort and time must be spent. However, nowadays a technology of automatic defect classification (ADC) is developed and the work of defect classification is performed by machines instead of human beings. For example, some defect inspection machines comprise an additional function of automatic defect classification. When the defect inspection 14 is done, the defect classification 16 is then performed to provide a report of defect inspection and grouping to the inline engineers for performing the following defect review 18 and defect analysis 22.

Normally, those defect classification machines are connected to a defect database which comprises a defect classification recipe stored therein to control the defect classification work. In other words, the accuracy of the defect classification is dependent on the classification recipe. However, since there are many differences between the defects caused by different processes, the methods of definition or classification of each defect type are also varied correspondingly. Thus, before an automatic defect classification is performed for the inline product, a defect database with proper defect classification recipe must be built so as to make the automatic defect classification machines work properly.

Please refer to FIG. 2, which is a schematic diagram of a conventional method of building a defect database in the prior art. As shown in FIG. 2, a sampling 32 is first performed to obtain a sample wafer. Then, a defect inspection, defect classification, and defect review are performed to collect defect information 34. After certain amounts of defect information of each defect type are collected, a database can be built according to this defect information. This defect information is used to train the defect classification machines and set a defect classification recipe 36. After that, an automatic defect classification can be performed according to the defect classification recipe. It is sure that at least one verifying step 38 is performed. According to a result of manual defect classification, the accuracy of the automatic defect classification can be judged or corrected before being put online 40.

As mentioned above, collecting the defect information 34 is needed before building a defect database in the conventional method. For improving the accuracy of the automatic defect classification, a large amount of defect samples must be reviewed by the SEM for collecting defect information. Normally, 30 to 50 defect samples are required for each defect type to build a defect database. Thus, taking a fabricating process generating 6 defect types as an example, 200 to 300 defect samples must be reviewed manually. It typically takes two months for building a defect database for a fabricating process. In addition, since defects of different defect types may have different probabilities of appearance, sometimes a defect type may have an extremely low probability of appearance. In that cases, a lot of test samples must be used for setting the defect classification recipe, leading to an increase of the handicap of building a defect database.

Furthermore, due to the progression of the semiconductor technology and some economic consideration, the size of wafers increases from 8 inches to 12 inches and the line width reduces from 0.18 µm to 0.13 µm and even below 0.1 µm. In the process from testing into mass production, it is obvious that the fabricating processes have to be changed or tuned many times in a short time. However, the conventional method of building a defect database always requires lots of time, leading to a delay of the defect root cause analysis. Thus, a quick and accurate method of building a defect database is strongly required to solve the aforementioned problems.

SUMMARY OF INVENTION

It is therefore a primary objective of the claimed invention to provide a quick and accurate method of building a defect database to solve the aforementioned problems in the prior art.

In a preferred embodiment of the claimed invention, a method of building a defect database is disclosed. First, a wafer with a plurality of defects thereon that were generated during a first semiconductor process is provided. A defect inspection is performed to detect the defects on the wafer. Then, an automatic defect classification is performed to separate the defects into a plurality of defect types according to a predetermined defect database having a defect classification recipe corresponding to a second semiconductor process. A manual defect classification is also performed to separate the defects into the plurality of defect types. After that, a verifying process is further performed by comparing the result of the automatic defect classification with that of a manual defect classification to verify the accuracy of the automatic defect classification. The second semiconductor process is a previous generation process compared to the first semiconductor process with the same design rule, or a process with similar patterns or the same defect types in comparison with the first semiconductor process.

It is an advantage that the claimed invention uses a present defect database as a basement and updates the defect database according to the collected defect information to improve the accuracy of the automatic defect classification, thereby shortening the building time of the defect database significantly.

These and other objectives of the claimed invention will no doubt become obvious to those of ordinary skill in the art after reading the following detailed description of the preferred embodiment which is illustrated in the various figures and drawings.

DETAILED DESCRIPTION

Figure 1:
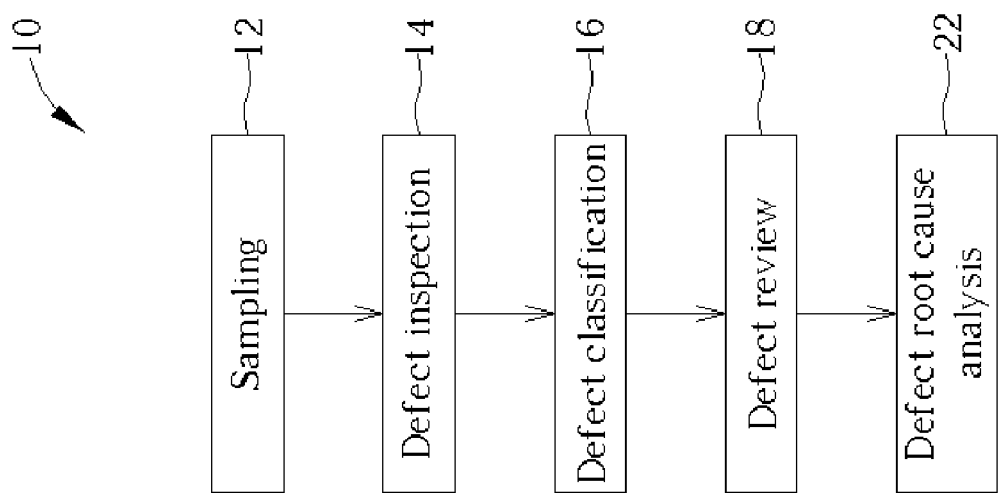
FIG. 1 is a schematic diagram of a prior art method of defect root cause analysis.
Figure 2:
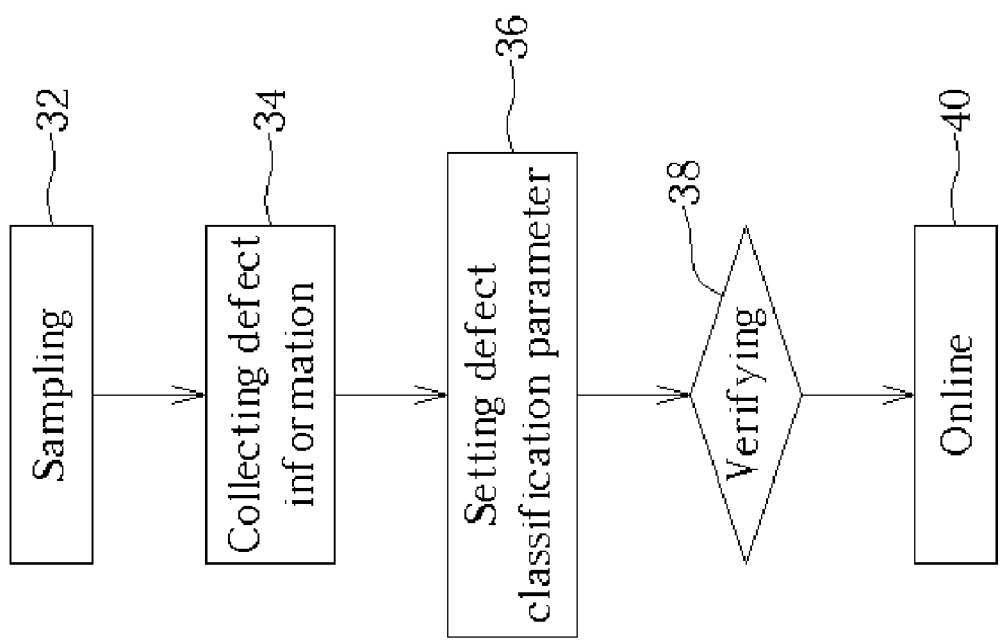
FIG. 2 is a schematic diagram of a conventional method of building a defect database in the prior art.
Figure 3:
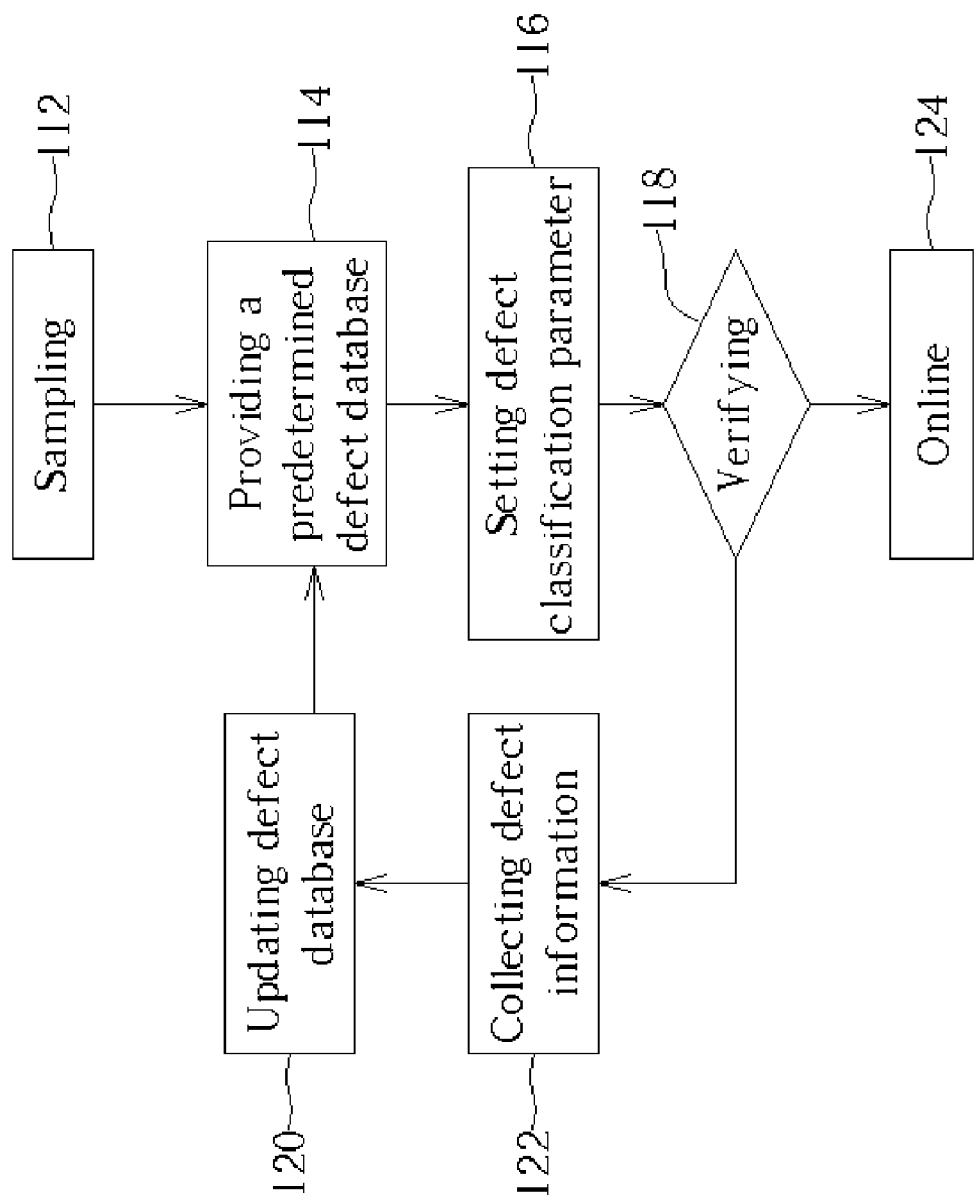
FIG. 3 is a schematic diagram of a method of building a defect database in the present invention.

Please refer to FIG. 3, which is a schematic diagram of a method of building a defect database in the present invention. As shown in FIG. 3, a sampling 112 is first performed to obtain a sample wafer with a plurality of defects that were generated in a first semiconductor process. Followed by a step of providing a predetermined defect database 114 corresponding to a second semiconductor process and a step of setting a defect classification recipe 116 according to the predetermined defect database, an automatic defect classification can be performed. Then, a verifying step 118 is performed to judge the accuracy of the automatic defect classification.

As aforementioned in the prior art technology, the verifying step 118 is performed by comparing the result of the automatic defect classification with that of a manual defect classification, which is treated as a standard. When the result of the automatic defect classification matches that of the manual defect classification, the defect database can be used online 124 and applied to the online defect classification machines. When the result of the automatic defect classification is different from that of the manual defect classification, an importance of the difference can be further judged by engineers. For example, if a result of an automatic defect classification has a smaller amount of defects of each defect type than that of the manual defect classification, but is still sensitive enough to detect the excursion cases such as a high amount of particles and to meet the requirement of the defect root cause analysis, the defect classification recipe can be accepted and applied to the machines online though there is still a difference between the automatic classification and the manual defect classification.

However, if the difference between the automatic classification and the manual defect classification is meaningful and cannot be neglected, a step of collecting defect information 122 can be performed as stated in the aforementioned description. In addition, if the database only has a poor identifying ratio for a specific defect type, the step of collecting defect information 120 focusing on the specific defect types is then performed for updating the defect database 120. Typically, the identifying ratio of the defect type can be improved significantly and becomes acceptable after collecting defect information of 5 to 10 samples. It is sure that the verifying step 118 is performed again until the defect database and the reset defect classification recipe can lead to an accurate automatic defect classification for the first semiconductor process.

It is noted that the predetermined defect database often has a high identifying ratio initially if the second semiconductor process is similar to the first semiconductor process. In a preferred embodiment of the present invention, the second semiconductor process is a previous generation process compared to the first semiconductor process with the same design rule or the first semiconductor process and the second semiconductor process have similar patterns or defect types. For example, if the first semiconductor process is a gate etching process of a 0.13 µm process, then the second semiconductor process can be chosen as a gate etching process of a previous generation, such as a 0.15 µm process, which has the same design rule as the first semiconductor process or a gate spacer etching process, which has similar patterns and defect types, to obtain a high initial accuracy of the classification. Sometimes no additional adjustment is required if the second semiconductor process is chosen properly. In most cases, the additional adjustment can be done by collecting defect information of a few defect samples, and a database corresponding to the first semiconductor process can be built successfully in a very short time, such as 3 to 5 days.

In contrast to the prior art, the method of building a defect database of the present invention utilizes a given defect database and a mechanism of defect database updating to adjust the defect classification recipe in the defect database. Thus, a reliable and accurate defect database can be obtained in a very short time to speed up the defect root cause analysis and improve the stability and the reliability of products.

Those skilled in the art will readily observe that numerous modifications and alterations of the device may be made while retaining the teaching of the invention. Accordingly, the above disclosure should be construed as limited only by the metes and bounds of the appended claims.

The invention claimed is:

1. A method of building a wafer defect database, the wafer defect database comprising a defect classification recipe which is used for a defect classification machine to perform an automatic defect classification, the method of building the defect database comprising following steps:

(a) providing a first wafer with a plurality of defects thereon that were generated during a first semiconductor process;

(b) performing a defect inspection to the first wafer to detect the defects;

(c) providing a predetermined defect database which comprises a defect classification recipe corresponding to a second semiconductor process;

(d) utilizing the defect classification machine to perform an automatic defect classification according to the predetermined defect database to separate the defects into a plurality of defect types;

(e) performing a manual defect classification to verify the accuracy of the automatic defect classification to each defect type;

(f) assigning the predetermined defect database as the wafer defect database when the accuracy of the automatic defect classification is qualified and setting up the predetermined database for online usage;

(g) performing an updating step to correct the predetermined defect database when the accuracy of a specific defect type of the automatic defect classification is not qualified, wherein the updating step comprises:
  providing a second wafer with a plurality of defects, wherein the second wafer was generated from the first semiconductor process;
  performing a defect inspection to the second wafer; and
  collecting defect classification recipe of the specific defect type to correct the defect classification recipe within the predetermined defect database; and
(h) repeating steps (d), (e), (f), and (g) to complete the wafer defect database.

2. The method of claim 1 wherein the second semiconductor process is a previous generation process compared to the first semiconductor process with the same design rule.

3. The method of claim 1 wherein the first semiconductor process and the second semiconductor process have similar patterns or defect types.

4. A method of an automatic wafer defect classification comprising:
  providing a wafer with a plurality of defects thereon that were generated during a first semiconductor process;
  performing a defect inspection to detect the defects;
  providing a defect database which comprises a defect classification recipe corresponding to a second semiconductor process; and
  performing an automatic defect classification according to the defect recipe to separate the defects into a plurality of defect types.

5. The method of claim 4 further comprising a verifying step to verify accuracy of the automatic defect classification for each defect type, the verifying step comprising:
  performing a manual defect classification to the defect; and
  utilizing the result from the manual defect classification to verify the accuracy of the automatic defect classification.

6. The method of claim 5 further comprising a step of updating the defect database if the accuracy of the automatic defect classification is not qualified, the step comprising:
  collecting defect information from another wafer respective to the classification type with unqualified accuracy according to the result of the manual defect classification;
  correcting the defect database according to the defect information; and
  repeating the verifying step.

7. The method of claim 4 wherein the second semiconductor process is a previous generation process compared to the first semiconductor process with the some design rule.

8. The method of claim 4 wherein the first semiconductor process and the second semiconductor process have similar patterns or defect types.

* * * * *